United States Patent [19]
Croisier

[11] 3,931,204
[45] Jan. 6, 1976

[54] THIENO[3,4-D]PYRIMIDINES
[75] Inventor: Paul Croisier, Waterloo, Belgium
[73] Assignee: U.C.B. Societe Anonyme, Belgium
[22] Filed: Jan. 17, 1974
[21] Appl. No.: 434,116

[30] Foreign Application Priority Data
July 14, 1970  United Kingdom............ 34144/70

Related U.S. Application Data
[62] Division of Ser. No. 162,255, July 13, 1971, Pat. No. 3,850,919.

[52] U.S. Cl.... 260/256.5 R; 260/251 A; 260/251 R; 260/247.1 L; 424/248; 424/251
[51] Int. Cl.$^2$........................................ C07D 239/00
[58] Field of Search ............................ 260/256.5 R

[56]  References Cited
UNITED STATES PATENTS
3,272,811  9/1966  Ohnacker et al. ............... 260/247.1
3,850,919  11/1974  Croisier..................... 260/247.1 L OTHER PUBLICATIONS
Chemical Abstracts Robba et al. 69:27365j (1968).

*Primary Examiner*—Leonard Schenkman
*Attorney, Agent, or Firm*—Wenderoth, Lind & Ponack

[57] ABSTRACT
Thieno[3,4-d]pyrimidines of the general formula:

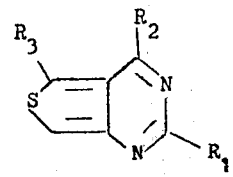

wherein $R_1$ is hydrogen, halogen, alkyl, alkoxy, amino, alkylamino, allylamino, hydroxy-alkylamino, cycloalkylamino, phenylamino, dialkylamino, di(hydroxyalkyl)-amino, alkyl-hydroxyalkyl-amino, pyrrolidino, piperidino, alkylpyrrolidino, alkylpiperidino, morpholino, alkyl-2-morpholino, alkyl-3-morpholino, dialkyl-3,5-morpholino, N-methylpiperazino, all said alkyl having 1 to 7 carbon atoms, said alkoxy having 1 to 5 carbon atoms and said cycloalkyl having 3 to 6 carbon atoms, $R_2$ has the same meanings as $R_1$ except alkyl and with the proviso that $R_2$ is other than hydrogen or halogen, when $R_1$ represents hydrogen or halogen and $R_3$ is hydrogen or alkyl having 1 to 7 carbon atoms, as well as the addition salts thereof with pharmaceutically acceptable acids are, in particular, active on the cardiovascular system. Processes for their preparation are given.

7 Claims, No Drawings

THIENO[3,4-D]PYRIMIDINES

This is a division of application Ser. No. 162,255, filed July 13, 1971 now U.S. Pat. No. 3,850,919.

The invention relates to new thieno[3,4-d]pyrimidines corresponding to the general formula (I):

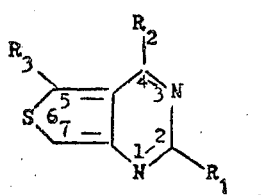

in which
$R_1$ = H, halogen, alkyl, alkoxy, amino, alkylamino, allylamino, hydroxyalkylamino, cycloalkylamino, phenylamino, dialkylamino, di-(aydroxyalkyl)-amino, alkyl-hydroxyalkyl-amino, pyrrolidino, piperidino alkylpyrrolidino, alkylpiperidino, morpholino, alkyl-2-morpholino, alkyl-3-morpholino, dialkyl-3,5-morpholino, N-methyl-piperazino, $R_2$ = all the meanings of $R_1$ except alkyl, with the proviso that $R_2$ is other than H or halogen when $R_1$ represents either H or halogen, $R_3$ = H or a $C_1$-$C_7$ alkyl radical, and their addition salts with pharmaceutically acceptable acids.

It also relates to the preparation of these compounds and their use as medicaments, either alone or in association with appropriate excipients.

As used herein, the term "alkyl" designates straight or branch chained radicals having 1 to 7 carbon atoms; the term "alkoxy" designates straight or branch chained radicals having 1 to 5 carbon atoms; and the term "cycloalkyl" designates radicals having 3 to 6, preferably 5 to 6 carbon atoms.

The thieno[3,4-d]pyrimidine system is a recent acquisition in chemistry. Synthesized for the first time by B. R. BAKER et al. (J.Org.Chem.18,(1953),138), it has been prepared subsequently by R. GOMPER et al. (Ann.659,(1962),90) and by ROBBA et al. (C.R.267, (1968,n°11),697).

It will, however, be observed that the processes of synthesis used by these authors only make it possible to obtain thieno[3,4-d]pyrimidin-4(3H)-ones unsubstituted in the 2-position. Furthermore the physiological properties of the thieno[3,4-d]pyrimidin-4(3H)-ones thus synthesized have not been examined by their authors; except for the antimalarial activity of a thieno[3,4-d]pyrimidin-4(3H)-ones substituted on the lactam nitrogen atom.

The $R_1$, $R_2$, $R_3$-substituted thieno[3,4-d]pyrimidines in accordance with the present invention may be prepared by one or other of the following processes:

a. reacting a 2,4-dihalo-5-$R_3$-thieno[3,4-d]pyrimidino of the formula (II) with a compound $R_2M$ (III), in accordance with the equation:

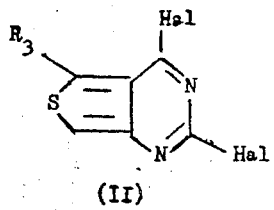

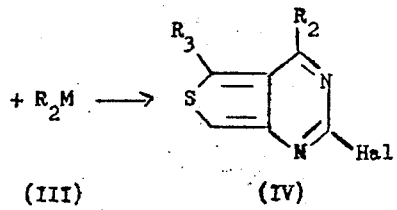

In these formulae
Hal = halogen
M = H or an alkali or alkaline-earth metal,
$R_2$ = unsubstituted amino, mono-substituted or di-substituted amino or heterocyclic radicals listed above when M = H, whereas when M is an alkali or alkaline-earth metal, $R_2$ = a $C_1$-$C_5$ alkoxy radical,
$R_3$ = has the meaning given above.

b. hydrogenolyzing the 2-halo-4-$R_2$-5-$R_3$-thieno[3,4-d]pyrimidine of the formula (IV), to obtain the corresponding 2-hydrogenated compound according to the equation:

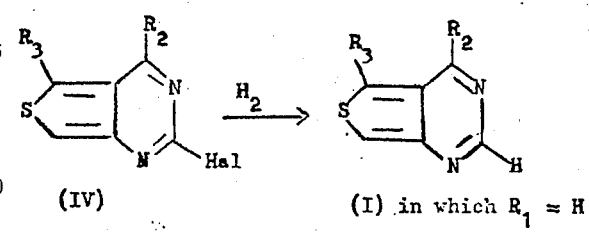

In these formulae
$R_2$ = alkoxy, unsubstituted amino, mono-substituted or disubstituted amino or heterocyclic radicals mentioned above,
Hal = halogen
$R_3$ has the meaning given above.

The nuclear magnetic resonance study of the derivatives obtained by the above-mentioned hydrogenolysis shows that the substitution during process (a) takes place in position 4 and not in position 2. In this last case, after hydrogenolysis, a long distance intercyclic coupling between the thiophenic proton 7 and the pyrimidinic proton 4 should have been observed (M. ROBBA et al., Bull.Soc. Chim.Fr.10,(1970),3630):

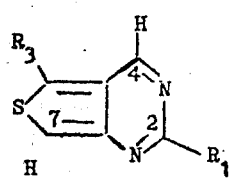

The absence of such a coupling consequently confirms the substitution in position 4.

c. reacting the 2-halo-4-$R_2$-5-$R_3$-thieno[3,4-d]pyrimidine of the formula (IV) with a compound $R_1M$ (V) according to the equation:

(IV) + $R_1M$ ⟶ (I)

(V)

In these formulae
Hal = halogen
M = H or an alkali or alkaline-earth metal,
$R_1$ = unsubstituted amino, mono-substituted or disubstituted amino or heterocyclic radicals mentioned above when M = H, whereas when M = an alkali or alkaline-earth metal, $R_1$ = a $C_1$–$C_5$ alkoxy radical,
$R_2$ = unsubstituted amino, mono-substituted or disubstituted amino or heterocyclic radicals mentioned above; it may also be a $C_1$–$C_5$ alkoxy radical provided $R_1$ is alkoxy and M is then an alkali or alkaline-earth metal,
$R_3$ = has the meaning given above.

d. when in the formula (I) $R_1$ and $R_2$ are identical and represent an amino group, a mono-substituted or disubstituted amino group or the heterocyclic radicals mentioned above, reacting a 2,4-dihalo-5-$R_3$-thieno[3,4-d]pyrimidine of the formula (II) with an excess of amine of the formula $R_1H$ or $R_2H$ (VI or VII) according to the equation:

(II) + $R_1H(=R_2H)$ ⟶ (I)

(VI) or (VII)

In these formulae
Hal = halogen
$R_1 = R_2$ = unsubstituted amino, mono-substituted or disubstituted amino or heterocyclic radicals mentioned above,
$R_3$ has the meaning given above.

e. when in the formula (I) $R_1$ and $R_2$ are identical and represent a $C_1$–$C_5$ alkoxy group, reacting a 2,4-dihalo-5-$R_3$-thieno[3,4-d]pyrimidine of the formula (II) with an excess of an alkali metal or alkaline-earth metal alcoholate of the formula $R_1M$ or $R_2M$ (VIII or IX) according to the equation:

(II) + $R_1M(=R_2M)$ ⟶ (I)

(VIII) or (IX)

In these formulae
Hal = halogen
M = an alkali or alkaline-earth metal
$R_1 = R_2 = C_1$–$C_5$ alkoxy
$R_3$ = has the meanings given above.

f. reacting a 2,4-dialkoxy-5-$R_3$-thieno[3,4-d]pyrimidine of formula (X) with an amine $R_2H$ (VII) according to the equation:

(X) + $R_2H$ ⟶ (XI)

(VII)

(X) = (I) in which
$R_1 = R_2$ = OAlk (XI) = (I) in which
$R_1$ = alkoxy

In these formulae
OAlk = $C_1$–$C_5$ alkoxy $R_2$ = unsubstituted amino, monosubstituted or disubstituted amino or heterocyclic radicals mentioned above, $R_3$ = has the meaning given above.

The identity of the products obtained by this process and of those obtained by process (c) in which $R_1$ = alkoxy, justifies the reaction equations and formulae as they are proposed for this process.

g. reacting a 2-$R_1$-4-halo-5-$R_3$-thieno[3,4-d]pyrimidine of the formula (XII) with a compound $R_2H$ (VII) according to the equation:

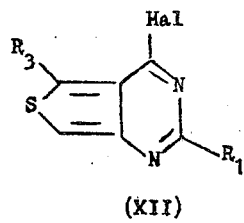

(XII)

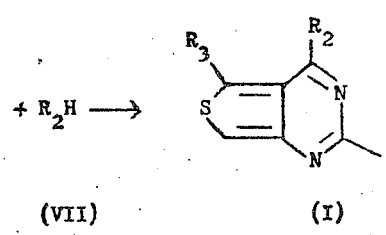

(VII)  (I)

In these formulae

Hal = halogen, $R_1$ = alkyl $R_2$ = lower alkoxy, unsubstituted amino, monosubstituted or disubstituted amino or heterocyclic radicals mentioned above, $R_3$ has the meaning given above.

The compounds according to the invention possess pharmaceutical properties of value, in particular cardiovascular effects.

The cardiovascular action was demonstrated particularly by the following pharmacological test: the blood rate in the thoracic aorta (cardiac output), in the vertebral artery (cerebral flow) and in the femoral artery (musculocutaneous peripheral flow) was measured in the dog anaesthetized with nembutal and subjected to artificial respiration.

The measurements were carried out by means of periarterial probes according to the principle of electromagnetic flow measurement. The general experimental conditions have already been described in the Literature (D. WELLENS and E. WAUTERS, Arch.Int.Pharmacod.171/1,(1968), 246). The medicament was administered by intravenous route.

The administration of compounds according to the invention, namely the 2-chloro-4-isopropylaminothieno[3,4-d]pyrimidine monohydrochloride (compound A), the 2-chloro-4-morpholino-thieno[3,4-d]pyrimidine monohydrochloride (compound B), the 2-chloro-4-(3-methyl-morpholino)-thieno[3,4-d]pyrimidine monohydrochloride (compound C), the 2-n-propylamino-4-isopropylamino-thieno[3,4-d]-pyrimidine monomaleate (compound D) and the 2-n-propyl-4-isopropylamino-thieno[3,4-d]pyrimidine mono-maleate (compound E) brought about the following effects under these conditions:

The compounds A, B and E, at a dose of 2 mg/kg. animal body weight, bring about an appreciable increase in the cardiac, cerebral and femoral flows; the compounds C and D, administered at the same dose, bring about an appreciable increase in the cardiac flow and a marked increase in the cerebral and femoral flows; the cerebral circulation increases in particular by 30 to 40% for at least 40 minutes. Respiratory analeptic action was demonstrated in rabbit, in morphinic respiratory depression. Under these conditions, the 2-ethoxy-4-isopropylamino-thieno[3,4-d]pyrimidine monohydrochloride (compound F) and the 2-ethoxy-4-n-propylamino-thieno[3,4-d]pyrimidine monohydrochloride (compound G), at the dose of 2,5 mg of free base/kg animal body weight, have an effect equivalent to that produced by a six times higher dose of diethylnicotinamide.

The intravenously administered lethal doses ($LD_{50}$) were determined in rat and mouse. For compounds A to G mentioned above, the recorded results, expressed in mg of compound per kg of animal body weight, are given in the following Table:

| Compound | Solvent | $LD_{50}$ rat | $LD_{50}$ mouse |
|---|---|---|---|
| A | propylene glycol + water | 65 | — |
| B | polyethylene glycol + ethanol | 130 | — |
| C | water | 109 | 117 |
| D | glycofurol | 25,5 | 21 |
| E | polyethylene glycol | — | 23 |
| F | water | 49 | — |
| G | water | 42 | — |

The compounds according to the invention may be administered by oral, parenteral or rectal route, in association with a pharmaceutical support or appropriate excipient.

Thus, in the case of oral administration, the forms may be solid or liquid and be presented in the form of capsules, coated or uncoated tablets, dragees, solutions or suspensions, in association with the supports or excipients generally used in pharmacy. The excipients for tablets include lactose, potato or corn starch, talcum, gelatin, cellulose, sugar, silica, magnesium or calcium stearate, polyvinylpyrrolidone and various colouring materials and aromas.

For parenteral administration, the support or excipient may be a parenterally acceptable sterile liquid, for example water, a solution of polyvinylpyrrolidone, or again a parenterally acceptable oil, for example groundnut oil.

For rectal administration, the support may be a base component for suppositories, for example cocoa butter or a mixture of glycerides.

The form of administration may be presented advantageously in unit doses.

The tablets, dragees, capsules, ampoules and suppositories preferably contain a unit dose of between 5 and 160 mg.

The solutions and suspensions preferably contain 0.1 to 1% by weight of active substance according to the invention, but they may contain up to 10% by weight.

The examples which follow illustrate the present invention without limiting it.

EXAMPLE 1.

Preparation of 2-chloro-4-isopropylamino-thieno[3,4-d]pyrimidine.

45 g (0.22 moles) of 2,4-dichloro-thieno[3,4-d]pyrimidine are suspended in 1800 ml of absolute ethyl alcohol. To the cooled mixture 28.5 g (0.48 moles) of isopropylamine are added drop by drop whilst agitating vigorously and maintaining the temperature at between 0° and 5°C. A clear solution is obtained which is agitated for a further hour at ambient temperature. The solution is concentrated, making sure that the temperature of the bath does not exceed 30°C. The syrupy residue is poured into iced water whilst agitating well. A yellow solid is formed which is drained off, washed with water and dried. 49 g of 2-chloro-4-isopropylamino-thieno[3,4-d]pyrimidine are obtained with a yield reaching 98% of theory. M.P. : 189°–191°C.

Analysis: $C_9H_{10}ClN_3S$ (molecular weight - M.W. : 227.7)

calculated (%): C 47.49 H 4.42 N 18.44 Cl 15.57 S 14.08 found (%): 47.50 4.64 18.44 15.32 14.07

This product is easily converted into the monohydrochloride in a known manner.

M.P. : 220°C (decomposes):

Analysis: $C_9H_{10}ClN_3S \cdot HCl$ (M.W.: 264.1)

calculated (%): N 15.89 Cl 26.84 S 12.14 found (%): 15.70 27.10 11.75

The following compounds of the invention are prepared in the same way:
- 2-chloro-4-propylamino-thieno[3,4-d]pyrimidine M.P. 134°–136°C. (recrystallized from toluene)
- 2-chloro-4-isobutylamino-thieno[3,4-d]pyrimidine M.P. 64°C. (not recrystallized)
- 2-chloro-4-(sec-butylamino)-thieno[3,4-d]pyrimidine M.P. 165°–169°C. (recrystallized from toluene)
- 2-chloro-4-[N-(1,5-dimethylhexyl)-amino]-thieno[3,4-d]pyrmidine M.P. 110°–113°C. (not recrystallized)
- 2-chloro-4-[N-(1-hydroxymethyl-ethyl)amino]-thieno[3,4-d]pyrimidine; M.P. 177°–178°C. (not recrystallized)
- 2-chloro-4-[N-(1-hydroxymethyl-2-hydroxy-ethyl)-amino]-thieno[3,4-d]pyrimidine; M.P. 174°–175°C. (recrystallized from acetone)
- 2-chloro-4-diethylamino-thieno[3,4-d]pyrimidine; M.P. 96°–97°C. (recrystallized from ethyl acetate-hexane mixture)
- 2-chloro-4-[di(2-hydroxyethyl)-amino]-thieno[3,4-d]pyrimidine; after recrystallization from acetone M.P. 145°C. (decomposes)
- 2-chloro-4-cyclopentylamino-thieno[3,4-d]pyrimidine; M.P. 148°–149.5°C. (recrystallized from benzene)
- 2-chloro-4-cyclopropylamino-thieno[3,4-d]pyrimidine; after recrystallization from benzene M.P. 113°C. (decomposes)
- 2-chloro-4-anilino-thieno[3,4-d]pyrimidine; M.P. 180°–182°C. (recrystallized from benzene)
- 2-chloro-4-pyrrolidino-thieno[3,4-d]pyrimidine; M.P. 131°–133°C. (not recrystallized)
- 2-chloro-4-piperidino-thieno[3,4-d]pyrimidine; M.P. 90°–94°C. (recrystallized from benzene)
- 2-chloro-4-morpholino-thieno[3,4-d]pyrimidine; M.P. 133°–135°C. (recrystallized from acetone)
- 2-chloro-4-(2-methyl-morpholino)-thieno[3,4-d]pyrimidine; M.P. 95°–100°C. (not recrystallized)
- 2-chloro-4-(3-methyl-morpholino)-thieno[3,4-d]pyrimidine; M.P. 126°–128°C. (recrystallized from toluene-hexane mixture)
- 2-chloro-4-(4-methyl-piperazino)-thieno[3,4-d]pyrimidine; M.P. 119°–121°C. (recrystallized from ethyl acetate-hexane mixture)
- 2-chloro-4-morpholino-5-methyl-thieno[3,4-d]pyrimidine; M.P. of the hydrochloride 240°C. (decomposes)
- 2-chloro-4-(3-methyl-morpholino)-5-methyl-thieno[3,4-d]pyrimidine; M.P. of the hydrochloride 222°C. (decomposes).

If desired, the excess of reactional amine, which serves to neutralize the liberated hydrochloric acid, may in each case be replaced by an at least equivalent amount of triethylamine.

The 2,4-dichloro-thieno[3,4-d]pyrimidine used as a raw material for the synthesis of the compounds mentioned in Example 1 is a new compound prepared by the chlorination of 2,4-dihydroxy-thieno[3,4-d]pyrimidine with phosphorus oxychloride at reflux temperature in the presence of N,N-diethylaniline. The obtained product melts at 122°–128°C. It is purified by sublimation in vacuo. A very pure product is thus obtained with a yield of 70% with respect to the amount of the starting dichloro compound. M.P. 133°–134°C.

Analysis: $C_6H_2Cl_2N_2S$ (M.W. 205)

calculated (%): C 35.2 N 13.66 Cl 34.6 S 15.64 found (%): 35.6 13.66 34.6 15.54

In turn, 2,4-dihydroxy-thieno[3,4-d]pyrimidine, which is also a new compound, is obtained by heating under reflux 3-ureido-4-carbomethoxy-thiophene suspended in absolute ethyl alcohol with concentrated hydrochloric acid for 4 hours. Yield: 65%. M.P. >300°C.

Analysis: $C_6H_4N_2O_2S$ (M.W. 168.1)

calculated (%): C 42.8 H 2.40 N 16.66 S 19.05 found (%): 42.7 2.67 16.64 19.30

The 3-ureido-4-carbomethoxy-thiophene, which is also a new compound, is obtained in turn by adding an aqueous solution of potassium cyanate to an aqueous hydrochloric acid solution of 3-amino-4-carbomethoxy-thiophene hydrochloride. The reaction takes place at room temperature with a yield of 80%. M.P.: goes brown at 165°C. and melts at 197°C. with decomposition.

Analysis: $C_7H_8N_2O_3S$ (M.W. 200.2)

calculated (%): C 42.0 H 4.03 N 13.99 found (%): 42.3 4.56 13.53

The 3-amino-4-carbomethoxy-thiophene hydrochloride is known from the article by B. R. BAKER et al. in J.Org.Chem.18,(1953),138; it may be prepared by the process described in this article.

EXAMPLE 2.

Preparation of 2-chloro-4-ethoxy-thieno[3,4-d]pyrimidine.

6.15 g (0.03 mole) of 2,4-dichloro-thieno[3,4-d]pyrimidine are suspended in 250 ml. of absolute alcohol at 0°C. Whilst agitating constantly a solution of 0.03 mole sodium ethylate in ethyl alcohol is added drop by drop. The speed of addition is regulated in such a manner that the temperature of the reaction medium is maintained at between 0° and 5°C. One obtains a clear solution in which a precipitate is gradually formed. When the addition is completed, the agitation is continued for a further 2 hours at ordinary temperature. The reaction mixture is then poured into 2 liters of iced water and the precipitate formed is filtered off, washed with water and then dried in vacuo. After recrystallization from toluene, 5.2 g of 2-chloro-4-ethoxythieno[3,4-d]pyrimidine are obtained (81% of theory). M.P. 136°–140°C.

Analysis: $C_8H_7ClN_2OS$ (M.W. 214.7)
calculated (%): C 44.7 H 3.28 N 13.03 S 14.94 Cl 16.51
found (%): 44.2 3.52 13.13 14.95 16.70

EXAMPLE 3.

Preparation of 4-isopropylamino-thieno[3,4-d]pyrimidine.

15 g of zinc powder are introduced into a solution of 3.9 g (0.017 moles) of 2-chloro-4-isopropylaminothieno[3,4-d]pyrimidine in 150 ml. of absolute ethyl alcohol. 25 ml. of glacial acetic acid are then added drop by drop wilst agitating. When the addition is completed, the agitation is continued for a further 36 hours at ordinary temperature. The reaction mixture is filtered over hyflocel and the filtrate is poured into 700 ml. of iced water. The pH of the solution is adjusted to 8 with sodium hydroxide and it is extracted several times with ether. The ether phase is washed with water to pH 7, it is dried over sodium sulfate and it is then evaporated to dryness. 1.9 g of 4-isopropylamino-thieno[3,4-d]pyrimidine, still containing a little of the initial product, are obtained. After chromatographic separation and recrystallization from ethyl acetate, one obtains 0.8 g (25% of theory) of the purified product which melts at 230°C with decomposition.

Analysis: $C_9H_{11}N_3S$ (M.W. 193.28)
calculated (%): C 56.0 H 5.73 N 21.72
found (%): 56.1 5.88 21.72

EXAMPLE 4.

Preparation of 2-n-propylamino-4-isopropylamino-thieno[3,4-d]pyrimidine.

A solution of 13 g (0.057 moles) of 2-chloro-4-isopropylaminothieno[3,4-d]pyrimidine in 250 ml. of n-propylamine, is heated in an autoclave at 140°C for 6 hours. The reaction solution is evaporated in vacuo and the solid residue is taken up in ether. It is bleached with active charcoal and the solvent is then driven off in vacuo. After recrystallization from acetone, 9.05 g of 2-n-propylamino-4-isopropylamino-thieno[3,4-d]pyrimidine (63% of theory) are obtained. M.P. 116°–118°C.

The free base, dissolved in a minimum of ethyl alcohol, may be converted into the monomaleate by adding a concentrated solution of maleic acid in ethyl alcohol, and then adding ether. 9.7 g of maleate (73% of theory) are obtained. M.P. 189°C. (decomposes).

Analysis: $C_{12}H_{18}N_4S$. 1 $C_4H_4O_4$ (M.W. 366.4)
calculated (%): C 52.5 H 6.06 N 15.3 S 8.75
found (%): 52.6 6.08 15.2 8.99

The base may also be converted into the monohydrochloride by dissolving it in methyl alcohol, adding a solution of hydrochloric acid in methyl alcohol and then ether. The product obtained has a melting point of 183°–185°C.

Analysis: $C_{12}H_{18}N_4S$. 1 HCl (M.W. 286.8)
calculated (%): C 50.2 H 6.67 N 19.5
found (%): 49.8 6.75 19.1

EXAMPLE 5.

Preparation of 4-isopropylamino-2-morpholino-thieno[3,4-d]pyrimidine.

6 g (0.26 moles) of 2-chloro-4-isopropylamino-thieno[3,4-d]pyrimidine and 25 mls. of morpholine are mixed and then heated under reflux for 4 hours. The mixture is cooled and poured into water with vigorous agitation; a brown solid appears, which is separated by filtration, washed with water and put to dry. The product is converted into the maleate, which is recrystallized from acetone. The free base is obtained again by treatment with alkali and is this way one obtains 3.4 g of pure product. M.P. 202°C. with decomposition.

Analysis: $C_{13}H_{18}N_4OS$ (M.W. 278.4)
calculated (%): C 56.0 H 6.51 N 20.1 S 11.51
found (%): 55.9 6.50 20.0 11.63

EXAMPLE 6.

Preparation of 2,4-dimorpholino-thieno[3,4-d]pyrimidine. (maleate)

As in Example 1, 2,4-dichloro-thieno[3,4-d]pyrimidine is used as the starting product and it is reacted with an excess of morpholine by heating under reflux. When the cooled reaction mixture is introduced into water with agitation, a yellow solid separates out, which is washed with water and dried. The residue is dissolved in a minimum of benzene and a concentrated ethanolic solution of maleic acid is added and then ether. The maleate which is precipitated is recrystallized from absolute ethyl alcohol. Yield reaches 40% of theory. M.P. : 225°C. (decomposes).

Analysis: $C_{14}H_{18}N_4O_2S$. 1 $C_4H_4O_4$ (M.W. 422.5)
calculated (%): C 51.1 H 5.25 N 13.2 S 7.58
found (%): 51.0 5.32 13.1 7.73

EXAMPLE 7.

By the methods described in Examples 4 to 6, it is also possible to obtain the following compounds of the invention:

- 2-n-butylamino-4-isopropylamino-thieno[3,4-d]pyrimidine; M.P. of the maleate: 191°C. (decomposes)
- 2,4-di(isopropylamino)-thieno[3,4-d]pyrimidine; M.P. of the maleate: 174°–176°C.
- 2-isobutylamino-4-isopropylamino-thieno[3,4-d]pyrimidine; M.P. of the maleate: 195°C. (decomposes)
- 2-(4-methyl-piperazino)-4-isopropylamino-thieno[3,4-d]pyrimidine; M.P. of the free base: 145°–148°C.; M.P. of the dimaleate: 190°C. (decomp.)
- 2-anilino-4-isopropylamino-thieno[3,4-d]pyrimidine; M.P. of the maleate: 260°C. (decomposes)
- 2,4-di(n-propylamino)-thieno[3,4-d]pyrimidine; M.P. of the maleate: 185°C. (decomposes)
- 2-(4-methyl-piperazino)-4-n-propylamino-thieno[3,4-d]pyrimidine; M.P. of the free base: 177°–180°C.; M.P. of the dihydrochloride: 296°C. (decomp.)

- 2-n-propylamino-4-isobutylamino-thieno[3,4-d]pyrimidine; M.P. of the maleate: 181°–182°C.
- 2-n-propylamino-4-sec-butylamino-thieno[3,4-d]pyrimidine; M.P. of the free base: 147°–149°C.
- 2-n-propylamino-4-diethylamino-thieno[3,4-d]pyrimidine; M.P. of the free base: 115°–119°C.
- 2-n-propylamino-4-cyclopentylamino-thieno[3,4-d]pyrimidine; M.P. of the maleate: 178°C. (decomposes)
- 2-n-propylamino-4-pyrrolidino-thieno[3,4-d]pyrimidine; M.P. of the maleate: 184°C. (decomposes)
- 2-n-propylamino-4-morpholino-thieno[3,4-d]pyrimidine; M.P. of the maleate: 181°–183°C.
- 2-(4-methyl-piperazino)-4-morpholino-thieno[3,4-d]pyrimidine; M.P. of the free base: 165°–167°C.; M.P. of the dimaleate: 210°C. (decomp.)
- 2-pyrrolidino-4-morpholino-thieno[3,4-d]pyrimidine; M.P. of the maleate: 205°C. (decomposes)
- 2-n-propylamino-4-[N-(1-hydroxymethyl-ethyl)-amino]-thieno[3,4-d]pyrimidine; M.P. of the maleate: 205°C. (decomposes)
- 2-n-propylamino-4-[N-(1-hydroxymethyl-2-hydroxy-ethyl)-amino]-thieno[3,4-d]pyrimidine; M.P. of the hydrochloride: 192°C. (decomp.)
- 2-ethylamino-4-isopropylamino-thieno[3,4-d]pyrimidine; M.P. of the maleate: 174°–175°C.
- 2,4-di(anilino)-thieno[3,4-d]pyrimidine; M.P. of the hydrochloride: 245°C. (decomposes)

EXAMPLE 8.

Preparation of 4-isopropylamino-5-methyl-2-n-propylamino-thieno[3,4-d]pyrimidine.

A solution of 12 g (0.0496 moles) of 2-chloro-4-isopropylamino-5-methyl-thieno[3,4-d]pyrimidine in 250 ml. of n-propylamine is heated in an autoclave at 140°C for 6 hours. The reaction mixture is evaporated in vacuo, the residue is taken up in ehter and the insolubles are filtered off. After bleaching with active charcoal, the solvent is driven off in vacuo. 16.3 g of a dark red syrup are obtained.

The maleate is prepared by dissolving the syrup in the minimum quantity of absolute ethyl alcohol, adding a concentrated ethanolic solution of maleic acid, and then ether. After recrystallization from acetone, 13.7 g (72% of theory) of 4-isopropylamino-5-methyl-2-n-propylamino-thieno[3,4-d]pyrimidine maleate are obtained. M.P. 178°C. (decomposes).

Analysis: $C_{13}H_{20}N_4S$. 1 $C_4H_4O_4$ (M.W. 380.5)
calculated (%): N 14.72 C 53.5 H 6.31 S 8.42
found (%): 14.68 53.2 6.47 8.70

The 2-chloro-4-isopropylamino-5-methyl-thieno[3,4-d]pyrimidine used as the starting product is a new compound prepared, with a yield of 80% from 2,4-dichloro-5-methyl-thieno[3,4-d]pyrimidine and isopropylamine according to the process described in Example 1. M.P. 118°–119°C. (recrystallized from toluene).

Analysis: $C_{10}H_{12}N_3ClS$ (M.W. 241.75)
calculated (%): N 17.36 Cl 14.66 S 13.26 C 49.65 H 5.00
found (%): 17.52 14.85 13.50 49.3 4.79

The 2,4-dichloro-5-methyl-thieno[3,4-d]pyrimidine used above is also a new compound obtained from 2,4-dihydroxy-5-methyl-thieno[3,4-d]pyrimidine and phosphorus oxychloride at reflux temperature in the presence of N,N-diethyl-aniline. It is easily purified by sublimation. Yield of sublimed product: more than 83%. M.P. 134°–136°C.

Analysis: $C_7H_4Cl_2N_2S$ (M.W. 219.1)
calculated (%): N 12.80 C 38.35 H 1.84 S 14.62 Cl 32.35
found (%): 12.30 38.70 2.00 14.32 32.00

The 2,4-dihydroxy-5-methyl-thieno[3,4-d]pyrimidine used above is also a new compound prepared from 3-carbethoxy-2-methyl-4-ureido-thiophene by heating under reflux with concentrated hydrochloric acid in absolute ethyl alcohol. Yield reaches 70%. M.P. 300°C.

Analysis: $C_7H_6N_2O_2S$ (M.W. 182.2)
calculated (%): N 15.36 C 46.1 H 3.32 S 17.60
found (%): 15.39 45.9 3.51 17.45

The 3-carbethoxy-2-methyl-4-ureido-thiophene used above is also a new compound prepared from 4-amino-3-carbethoxy-2-methylthiophene hydrochloride and potassium cyanate in an aqueous hydrochloric acid medium. The reaction takes place at room temperature with a yield of 89%. M.P. 186°–192°C.

Analysis: $C_9H_{12}N_2O_3S$ (M.W. 228.3)
calculated (%): N 12.28 S 14.05 C 47.30 H 5.30
found (%): 12.26 14.36 47.7 5.38

The 4-amino-3-carbethoxy-2-methyl-thiophene hydrochloride is also a new compound prepared in ether at room temperature from 3-carbethoxy-4-hydroxyimino-2-methyl-tetrahydrothiophene and a solution of hydrochloric acid in ethyl alcohol. Yield: 40%. After recrystallization from a mixture of ethanol and ether, M.P. 185°C. (decomposes).

Analysis: $C_8H_{11}NO_2S.HCl$ (M.W. 221.7)
calculated (%): N 6.31 S 14.4 Cl 16.0 C 43.3 H 5.45
found (%): 6.36 14.2 16.3 43.2 5.63

Finally the 3-carbethoxy-4-hydroxyimino-2-methyl-tetrahydrothiophene is prepared in alcohol under reflux with a yield of 91% from the known compound 3-carbethoxy-2-methyl-4-oxo-tetrahydrothiophene (TAKAYA et al., Bull. Chem. Soc. Japan, 41,(1968),2086) and hydroxylamine hydrochloride in the presence of barium carbonate.

The 3-carbethoxy-4-hydroxyimino-2-methyl-tetrahydrothiophene is an oily product.

Analysis: $C_8H_{13}NO_3S$ (M.W. 203.3)
calculated (%): N 6.88 S 15.8
found (%): 6.96 15.6

EXAMPLE 9.

Preparation of 4-morpholino-2-n-propyl-thieno[3,4-d]pyrimidine.

3 g (0.014 moles) of 4-chloro-2-n-propyl-thieno[3,4-d]pyrimidine is added in small portions, with thorough agitation, to 12 ml. of morpholine cooled to 0°C. The speed of addition must be regulated in such a way that the temperature of the reaction mixture does not exceed 10°C. When the addition is completed, the mixture is allowed to return to ordinary temperature and the agitation is continued at this temperature for one hour. The mixture is allowed to stand for 24 hours and then is poured with agitation into 500 ml. of cold water. The solid which is precipitated is drained off, washed with water and dried. It is taken up in methyl alcohol, the methyl alcohol solution is bleached over active charcoal and the solvent is driven off in vacuo.

2.5 g (68% of theory) of 4-morpholino-2-n-propyl-thieno[3,4-d]pyrimidine are obtained. M.P. 102°–105°C.

Analysis: $C_{13}H_{17}N_3OS$ (M.W. 263.4)
calculated (%): C 59.2 H 6.50 N 15.9 S 12.17 found (%): 59.1 6.54 15.9 12.14

The monohydrochloride is prepared by dissolving the base in benzene, adding an anhydrous solution of hydrochloric acid in ethyl alcohol and then adding ether. M.P. 230°C. (decomposes).

Analysis: $C_{13}H_{17}N_3OS$. 1 HCl (M.W. 299.8)
calculated (%): N 14.0 S 10.69 Cl 11.82
found (%): 13.9 10.23 11.83

The following compounds were prepared in a similar manner:
- 2-n-propyl-4-(3-methyl-morpholino)-thieno[3,4-d]pyrimidine; M.P. of maleate: 144°–146°C. (recrystallized from isopropanol)
- 2-n-propyl-4-(4-methyl-piperazino)-thieno[3,4-d]pyrimidine; After recrystallization from ethanol M.P. of dimaleate: 189°C. (decomposes)
- 2-n-propyl-4-isopropylamino-thieno[3,4-d]pyrimidine;
  M.P. of free base: 137°–139.5°C. (recrystallized from ethylacetate);
  M.P. of maleate: 132°–134°C. (recrystallized from ethyl acetate).

The 4-chloro-2-n-propyl-thieno[3,4-d]pyrimidine used as starting material is a new compound prepared by heating for 2 hours at 60°C, 4-hydroxy-2-n-propyl-thieno[3,4-d]pyrimidine with phosphorus oxychloride in the presence of N,N-diethylaniline. Yield reaches 57%. M.P. 78°–80°C. (recrystallized from acetonitrile).

Analysis: $C_9H_9N_2ClS$ (M.W. 212.7)
calculated (%): N 13.16 S 15.07 Cl 16.66
found (%): 13.14 15.03 16.30

The 4-hydroxy-2-n-propyl-thieno[3,4-d]pyrimidine used above is also a new product prepared by the action of concentrated ammonia at room temperature on 2-n-propyl-4-oxo-4H-thieno[3,4-d]-m-oxazine. The pure product is obtained with a yield at 65%. M.P. 212°–214°C. (recrystallized from ethyl acetate).

Analysis: $C_9H_{10}N_2OS$ (M.W. 194.3)
calculated (%): C 55.6 H 5.19 N 14.41 S 16.50
found (%): 55.9 5.20 14.42 16.50

The 2-n-propyl-4-oxo-4H-thieno[3,4-d]-m-oxazine used above is also a new product prepared by the action of acetic anhydride at reflux temperature on 3-butanoylamino-4-thenoic acid. Yield is 50%. M.P.: 101°–103°C. (recrystallized from acetic anhydride)

Analysis: $C_9H_9NO_2S$ (M.W. 195.2)
calculated (%): N 7.17 S 16.42
found (%): 7.10 16.55

The 3-butanoylamino-4-thenoic acid used above is also a new product prepared by the selective hydrolysis of 3-butanoylamino-4-carbomethoxy-thiophene is a mixture of sodium hydroxide, water and methyl alcohol at ordinary temperature. Yield: 90%. M.P. 135°–138°C.

Analysis: $C_9H_{11}NO_3S$ (M.W. 213.2)
calculated (%): C 50.7 H 5.20 N 6.56 S 15.03
found (%): 50.9 5.21 6.63 15.11

The 3-butanoylamino-4-carbomethoxy-thiophene used above is also a new product prepared by the action of butyric anhydride on 3-amino-4-carbomethoxy-thiophene hydrochloride in the presence of pyridine at ordinary temperature. Yield: 80%. B.P. 120°–124°C./0.1 mm Hg.

Analysis: $C_{10}H_{13}NO_3S$ (M.W. 227.2)
calculated (%): C 52.8 H 5.76 N 6.16 S 14.1
found (%): 53.1 5.77 6.15 14.2

The 3-amino-4-carbomethoxy-thiophene hydrochloride is known from the article by B. R. BAKER et al. cited in Example 1 of the present invention.

EXAMPLE 10.

Preparation of 2,4-diethoxy-thieno[3,4-d]pyrimidine.

A solution of 0.06 mole sodium ethylate in ethyl alcohol is added dropwise while cooling to a suspension of 6.15 g (0.03 mole) of 2,4-dichloro-thieno[3,4-d]pyrimidine in 100 ml absolute ethyl alcohol. The speed of addition is regulated in such a way that the temperature of the reaction medium is maintained at between 0° and 5°C. When addition is completed, the solution is left to rise to room temperature and is then heated under reflux for 4 hours. It is then evaporated to dryness. The remaining solid is drained, washed with water and left to dry. AFter recrystallization from a 50/50 mixture of ethyl alcohol and water, 2.8 g (42% of theory) of 2,4-diethoxy-thieno[3,4-d]pyrimidine are obtained. M.P. 84°–86°C.

Analysis: $C_{10}H_{12}N_2O_2S$ (M.W. 224.3)
calculated (%): C 53.5 H 5.35 N 12.5 S 14.8
found (%): 53.2 5.44 12.6 14.5

- 2,4-dimethoxy-thieno[3,4-d]pyrimidine is prepared in the same way. M.P. 131°–132°C. (recrystallized from methyl alcohol).

EXAMPLE 11.

Preparation of 2-ethoxy-4-n-propylamino-thieno[3,4-d]pyrimidine.

A solution of 2.3 g (0.01 mole) of 2,4-diethoxy-thieno[3,4-d]pyrimidine and 3.6 g (0.06 mole) of n-propylamine in 50 ml absolute ethyl alcohol is heated under reflux for 10 hours. The solution is then evaporated to dryness. The solid is drained off, washed with water and dried. After recrystallization from toluene, 14 g (59% of theory) of 2-ethoxy-4-n-propylamino-thieno[3,4-d]pyrimidine are obtained. M.P. 140°–142°C.

Analysis: $C_{11}H_{15}N_3OS$ (M.W. 237.3)
calculated (%): N 17.72 S 13.5
found (%): 17.46 13.8

This product is easily converted into the hydrochloride in known manner. M.P. of the hydrochloride: 154°C. (decomposes)

Analysis: $C_{11}H_{15}N_3OS.HCl$ (M.W. 273.8)
calculated (%): N 15.34 S 12.9
found (%): 15.32 13.0

-2-ethoxy-4-isopropylamino-thieno[3,4-d]pyrimidine is prepared in the same way. M.P. of the free base: 154°–156°C.; M.P. of the hydrochloride: 166°C. (decomp.)

EXAMPLE 12.

Preparation of 2-ethoxy-4-isopropylamino-thieno[3,4-d]pyrimidine.

A solution of 4.5 g (0.02 mole) of 2-chloro-4-isopropylamino-thieno[3,4-d]pyrimidine and 0.02 mole sodium ethylate in 200 ml absolute ethyl alcohol is heated in an autoclave at 120°C. for 6 hours. It is then evaporated to dryness. The residue is taken up in a mixture of ether and water; the ether phase is washed with water till neutral pH, dried over $Na_2SO_4$, filtered and the solvent is driven off in vacuo. The remaining solid (4.4 g) is recrystallized from a mixture of ethyl acetate-hexane containing 30% ethyl acetate. 3.2 g (68% of theory) of 2-ethoxy-4-isopropylaminothieno[3,4-d]pyrimidine are obtained. M.P. 155°–156°C.
Analysis: $C_{11}H_{15}N_3OS$ (M.W. 237.3)
calculated (%): N 17.72 S 13.5
found (%): 17.44 13.9

This compound was compared with that prepared in Example 11 and which melted at 154°–156°C. The identity of both substances was confirmed by the test of mixture M.P. and by IR spectroscopy.

I claim:
1. A compound selected from the group consisting of
a. thieno[3,4-d]pyrimidines of the formula:

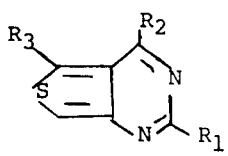

wherein $R_1$ is a member selected from the group consisting of hydrogen, chloro, alkyl, alkoxy, alkylamino, and phenylamino, all the alkyl groups having 1 to 7 carbon atoms, the alkoxy group having 1 to 5 carbon atoms, $R_2$ is a member selected from the group consisting of alkylamino, hydroxyalkylamino, cycloalkylamino, phenylamino, dialkylamino, di(hydroxyalkyl)-amino, all of the alkyl groups having 1 to 7 carbon atoms and the cycloalkyl group having 3 to 6 carbon atoms, and $R_3$ is a member selected from the group consisting of hydrogen and methyl and b. the addition salts thereof with pharmaceutically acceptable acids.

2. A compound according to claim 1, which is 2-chloro-4-isopropylaminothieno-[3,4-d]pyrimidine.

3. A compound according to claim 1, which is 2-n-propylamino-4-isopropylaminothieno[3,4-d]pyrimidine.

4. A compound according to claim 1, which is 2-n-propyl-4-isopropylaminothieno[3,4-d]pyrimidine.

5. A compound according to claim 1, which is 2-ethoxy-4-n-propylaminothieno[3,4-d]pyrimidine.

6. A compound according to claim 1, which is 2-ethoxy-4-isopropylaminothieno[3,4-d]pyrimidine.

7. A compound according to claim 1, which is 2-chloro-4-diethylamino-thieno[3,4-d]pyrimidine.

* * * * *